United States Patent
Kim et al.

(10) Patent No.: US 7,914,681 B2
(45) Date of Patent: *Mar. 29, 2011

(54) HEMODIALYZER CAPABLE OF INTERMITTENT REPETITION OF INFUSION AND WATER REMOVAL OPERATION

(75) Inventors: Sung-Teh Kim, Kitakyushu (JP); Kunihiko Yamanaka, Hiroshima (JP); Naritomi Maeda, Hiroshima (JP); Katsunori Masaoka, Hiroshima (JP)

(73) Assignee: JMS Co., Hiroshima (JP)

( * ) Notice: Subject to any disclaimer, the term of this patent is extended or adjusted under 35 U.S.C. 154(b) by 1061 days.

This patent is subject to a terminal disclaimer.

(21) Appl. No.: 11/597,804

(22) PCT Filed: May 28, 2004

(86) PCT No.: PCT/JP2004/007727
§ 371 (c)(1),
(2), (4) Date: Nov. 27, 2006

(87) PCT Pub. No.: WO2005/115498
PCT Pub. Date: Dec. 8, 2005

(65) Prior Publication Data
US 2009/0159515 A1    Jun. 25, 2009

(51) Int. Cl.
*A61M 1/34*    (2006.01)
(52) U.S. Cl. ........ 210/646; 210/138; 210/139; 210/141; 604/6.11; 604/5.01

(58) Field of Classification Search .................. 210/646, 210/138, 139, 141; 604/321.6, 5.01, 6.11
See application file for complete search history.

(56) References Cited

U.S. PATENT DOCUMENTS
7,780,848 B2 *   8/2010   Kim et al. ..................... 210/138

FOREIGN PATENT DOCUMENTS

| JP | 6-134031 | 5/1994 |
|----|----------|--------|
| JP | 7-313589 | 12/1995 |
| JP | 11-221275 | 8/1999 |
| JP | 3277569 | 4/2002 |
| JP | 2004-016675 | 1/2004 |
| JP | 3528597 | 5/2004 |

* cited by examiner

*Primary Examiner* — Terry K Cecil
(74) *Attorney, Agent, or Firm* — Jordan and Hamburg LLP (57) ABSTRACT

According to the present invention, there is provided a hemodiafiltration apparatus capable of easily and efficiently removing medium to large molecule solutes at a low cost. Provided is a hemodialysis apparatus which uses a hemodialyzer accommodating a hollow yarn membrane in hemodiafiltration to cause a dialysis fluid to flow from a dialysis fluid circuit side to a blood circuit side by forceful back-filtration via the hemodialyzer, and to cause a fluid in the blood circuit to reflux to a dialysis fluid circuit side by filtration via the hemodialyzer, the hemodialysis apparatus being characterized in that a flux operation of the fluid from the dialysis fluid side to the blood circuit side by the back-filtration, and a reflux operation of the fluid from the blood circuit side to the dialysis fluid circuit side by the filtration are repeated intermittently and for at least a plurality of times.

14 Claims, 4 Drawing Sheets

HEMODIALYZER CAPABLE OF INTERMITTENT REPETITION OF INFUSION AND WATER REMOVAL OPERATION

TECHNICAL FIELD

The present invention relates to a hemodialysis (filtration) apparatus, and in particular, to a blood purifier that efficiently removes wastes and moisture from a patient's body by performing filtration and back-filtration periodically and intermittently.

BACKGROUND ART

For a treatment of a patient suffering from renal failure, there have been proposed various blood purifying methods in which blood is taken out from the body of the patient to be purified and is then returned into the body. To purify the blood, hemodialyzers which accommodate a translucent membrane (hereinafter also referred to as "dialysis membrane") such as a hollow yarn cellulose membrane, polyacrylonitrile membrane, or polysulfone membrane in a housing have been used. The purification method to be employed differs according to a state of a disease and conditions of a patient.

For example, in case of hemodialysis (HD), blood and a dialysis fluid are brought into contact with each other through the dialysis membrane of the hemodialyzer to remove urea, uric acid, and the like accumulated in the blood of a patient by the movement of substances caused by diffusion. In a case of hemofiltration (HF), water, body wastes, and toxins in the blood are removed by filtration through holes provided in the dialysis membrane.

In the above-mentioned treatment method, HD (hemodialysis) has an excellent property of removing small-molecular wastes and solutes, but has a disadvantage of lacking performance of the removal of medium molecules and large molecules. Meanwhile, HF (hemofiltration) has an excellent property of removing medium (or large) molecular wastes, but has disadvantages in that a performance of removing small molecules is low and that proteins in blood are apt to leak. Moreover, both the HD and HF are greatly affected by the characteristics of the hollow yarn membrane in the hemodialyzer.

As a treatment method having the advantages of both the HD and HF, that is, excellent removal characteristics of the HD and HF, there has been proposed a hemodiafiltration (HDF) method, and efficient removal of a solute has been expected. However, in a conventional bottle-type HDF system, only about 5 to 10 L of fluid substitution can be performed, and hence, a remarkable effect could not be exhibited. Therefore, large-quantity fluid substitution HDF by on-line HDF or Push & Pull HDF has come to attract attention, and the former on-line HDF capable of constructing a system relatively easily has widely come into use.

As prior art documents, JP 06-134031 A, JP 07-313589 A, and the like shown below have been disclosed.

However, in order to perform HDF (including on-line HDF and Push & Pull HDF), a dedicated blood circuit for injecting a supplemental fluid (i.e., substitution fluid) has been required, and furthermore, in bottle-type HDF, it has been required to prepare a dedicated supplemental fluid.

In contrast, the present invention provides a hemodialysis apparatus which does not require a dedicated blood circuit or the preparation of a dedicated supplemental fluid and the like, and in which the HD treatment can be shifted to the HDF treatment easily, or the HDF treatment can be shifted to the HD treatment easily.

DISCLOSURE OF THE INVENTION

According to the present invention, the above-mentioned problems are solved by the following configuration.

That is, the configuration of the present invention relates to a hemodialysis apparatus 1, which uses a hemodialyzer 8 accommodating a hollow yarn membrane in hemodialysis (filtration) to cause a dialysis fluid to flow from a dialysis fluid supply circuit 12 side to a second blood circuit 11 side by forceful back-filtration by a control of at least one of fluid feed pumps P6 and P3 in association with each other via the hemodialyzer 8, and to cause a fluid in a first blood circuit 10 to reflux to a dialysis fluid discharge circuit 13 side by filtration via the hemodialyzer 8 in the same manner. The hemodialysis apparatus is characterized in that a flux operation (hereinafter, also referred to as "back-filtration operation") of the fluid from the dialysis fluid supply circuit 12 side to the second blood circuit side by the back-filtration, and a reflux operation (also referred to as "filtration operation") of the fluid from the first blood circuit 10 side to the dialysis fluid discharge circuit 13 side by the filtration are repeated intermittently and for at least a plurality of times.

In the specification of the present application, the processing of repeating a back-filtration operation and a filtration operation a plurality of times intermittently will be abbreviated as tidal HDF (Tidal: state where the flux and the reflux of a fluid are repeated in accordance with the flux and reflux of the tides) for convenience sake.

The hemodialysis (filtration) apparatus of the present invention has the above-mentioned configuration, so until a fluid fluxed in the body by back-filtration is taken out from the body by filtration, i.e., until a blood circulation system is connected to a dialysis fluid supply and discharge system via a dialyzer 8 to move the moisture of the blood circulation system to the dialysis fluid supply and discharge system by a pressure range, a time lag occurs. Therefore, a solute is removed (i.e., exchanged) after the fluid is permeated through cells or interstitial tissue of a patient. Consequently, the removing effect of a solute, or the removing effect of medium/large molecules is enhanced remarkably.

The use of the hemodialysis (filtration) apparatus of the present invention enhances the effect of filtration and enables the removal of medium and large molecular-weight substances. Further, by enhancing the filtration effect, the efficiency depending upon the hollow yarn membrane characteristics of the hemodialyzer can be improved.

Further, owing to the back-filtration, a substitution fluid fluxing in the blood circuit permeates the cells or interstitial tissue of a patient, and is removed after the substance exchange. Therefore, compared with the existing HDF and HF (in which the substitution and the removal of a fluid are performed at a body fluid level), the purifying efficiency of blood is enhanced remarkably.

BEST MODE FOR CARRYING OUT THE INVENTION

Hereinafter, the present invention will be described in detail by way of embodiments shown in the drawings.

Figure 1:
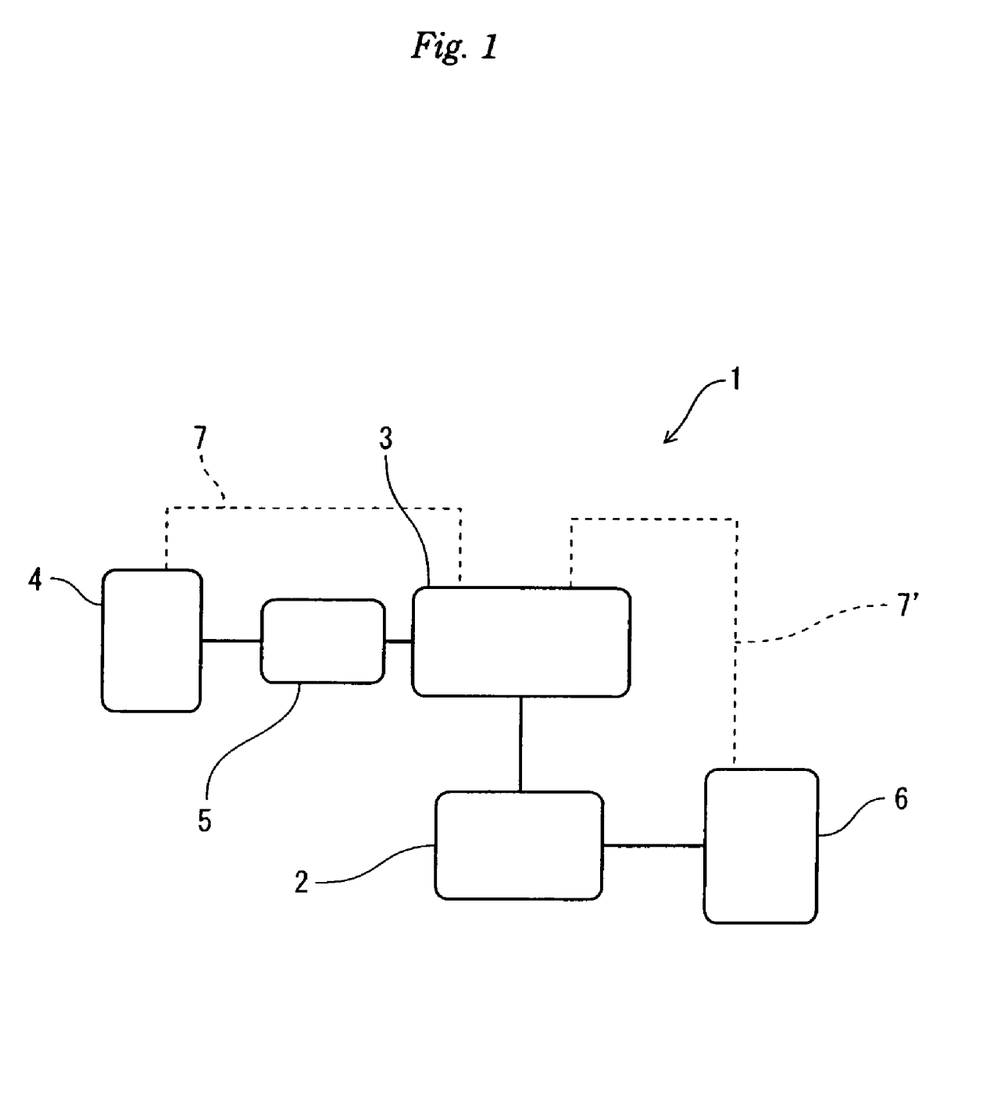
FIG. 1 is a block diagram schematically showing a configuration and control in an embodiment of a hemodialysis apparatus of the present invention.

FIG. 1 is a block diagram schematically showing a construction of an embodiment of a hemodialysis apparatus of the present invention. In FIG. 1, reference numeral 1 represents the hemodialysis apparatus. The hemodialysis apparatus 1 includes a dialysis working device 2, a control unit 3 for controlling the operation and processing of the hemodialysis apparatus 1, a blood input unit 4 for inputting instructions/conditions and operation, a display unit 5 for displaying an input state and a control mechanism, a monitor 6 for showing the operation state of the control unit, and the like.

The above-mentioned input unit 4 and the monitor 6 of the working device are connected to the control unit 3 by transmission systems 7 to enable the setting conditions to be changed by the input unit 4 while the operation state of the dialysis working device 2 is checked through the monitor 6, and to enable the operation of the dialysis working device 2 to be changed through the transmission systems 7 and the control unit 3. In FIG. 1, the input unit 4 and the monitor 6 are connected to the control unit 3 by the transmission systems 7. However, all of the above-mentioned input unit 4, the monitor 6, and the control unit 3 may be connected to the transmission system 7.

Details of the dialysis working device 2 will be described later according to FIG. 4. The dialysis working device 2 is provided with a device which is activated to carry out an actual hemodialysis treatment, such as a water discharge pump or a blood pump, a dialysis fluid supply unit or discharge unit, fluid paths such as a dialysis fluid circuit and a blood circuit, a channel opening and closing unit for opening and closing the fluid paths, and a hemodialyzer for carrying out filtration or back-filtration.

The input unit 4 for inputting processing conditions and instructions includes: a device for setting or changing the total filtration amount from a patient, the treatment time, and the amount of the reversely filtered fluid flowing into the body of the patient; a device for setting or changing the time required for one cycle including water removal and water injection (by back-filtration); or the like. Preferably, each of those conditions can be input and changed from one panel, but the present invention is not limited to this.

The display unit 5, from which an operator can check (grasp) the instructions and conditions of the above-mentioned input unit 4, their input states, and the control mechanism before the start of the dialysis working device 2, may be composed of a panel integrated with the input unit 4. As described above, the monitor 6 for monitoring the operation state of the dialysis working device 2 is connected to the dialysis working device 2, displays the operation state of the dialysis working device 2, and can finely adjust the dialysis working device 2 through the transmission systems 7 and the control unit 3 when the working device does not operate according to the preset conditions.

Figure 2:
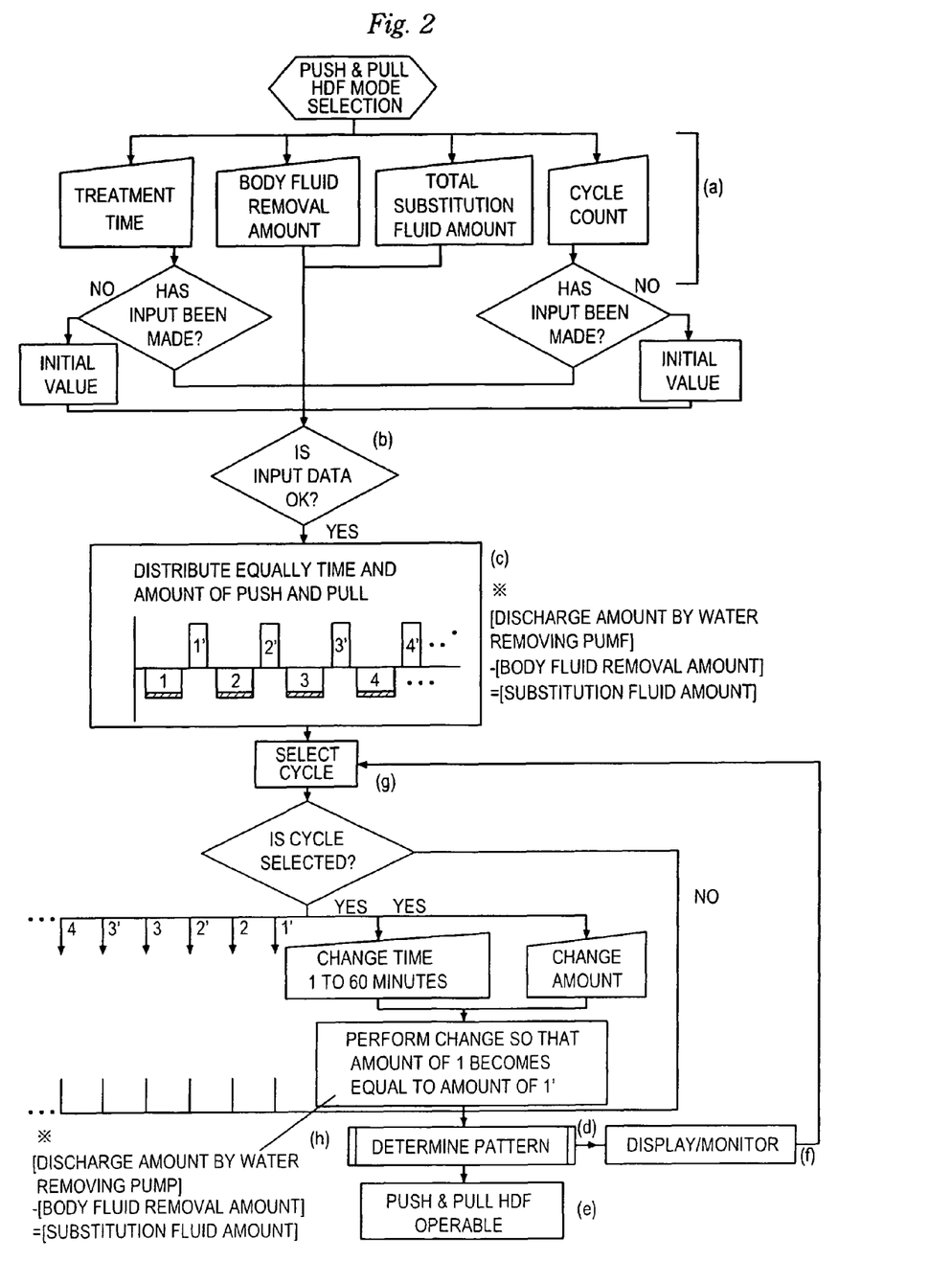
FIG. 2 is a flowchart schematically showing a flow of a processing operation by an exemplary hemodialysis apparatus of the present invention.

FIG. 2 is a flow chart showing a procedure for carrying out the hemodialysis process by means of the hemodialysis apparatus of the present invention, that is, all the steps including (a) the setting of conditions (input), (b) the confirmation of inputs, (c) the display of hemodialysis conditions, (d) confirmation and determination, (e) execution (hemodialysis process), (f) the monitoring of the operation state of the dialysis apparatus, (g) adjustment and alteration, and (h) feedback control to the dialysis apparatus.

First, the amount of the removed body fluid, the treatment time, and the total amount of the injected substitution fluid (i.e., the amount of the reversely filtered fluid flowing into the body of the patient, also referred to as "total amount of substitution fluid") are set and input to the input unit 4. Each cycle, which is composed of the injection of the substitution fluid from the hemodialyzer by back-filtration and the removal of water by filtration within the time required for carrying out hemodialysis, is defined as one cycle. Then, whether how many cycles in total are to be repeated is set. Since the treatment time per cycle is the time required for carrying out each cycle, that time may be set. For example, the time per cycle can be adjusted within a range from 1 minute to 60 minutes.

If input restrictions are set in the hemodialysis apparatus so that the relationship between the time of the substitution fluid injection by back-filtration and the time of water removal by the filtration within one cycle always becomes [time of substitution fluid injection]<[time of water removal], the removal of the solute or the purification of the blood can be carried out efficiently without applying stress to the living body. If input restrictions are set in the hemodialysis apparatus to satisfy the expression |amount of injected substitution fluid|+|amount of water removed from patient|=|total filtration amount| with respect to the relationship between the amount of the injected substitution fluid and the amount of the removed water, the amount of a fluid discharged by the water removing pump is calculated automatically by setting the amount of the injected substitution fluid and the amount of the removed body fluid, and the water removing pump is controlled, which is convenient.

Figure 3:
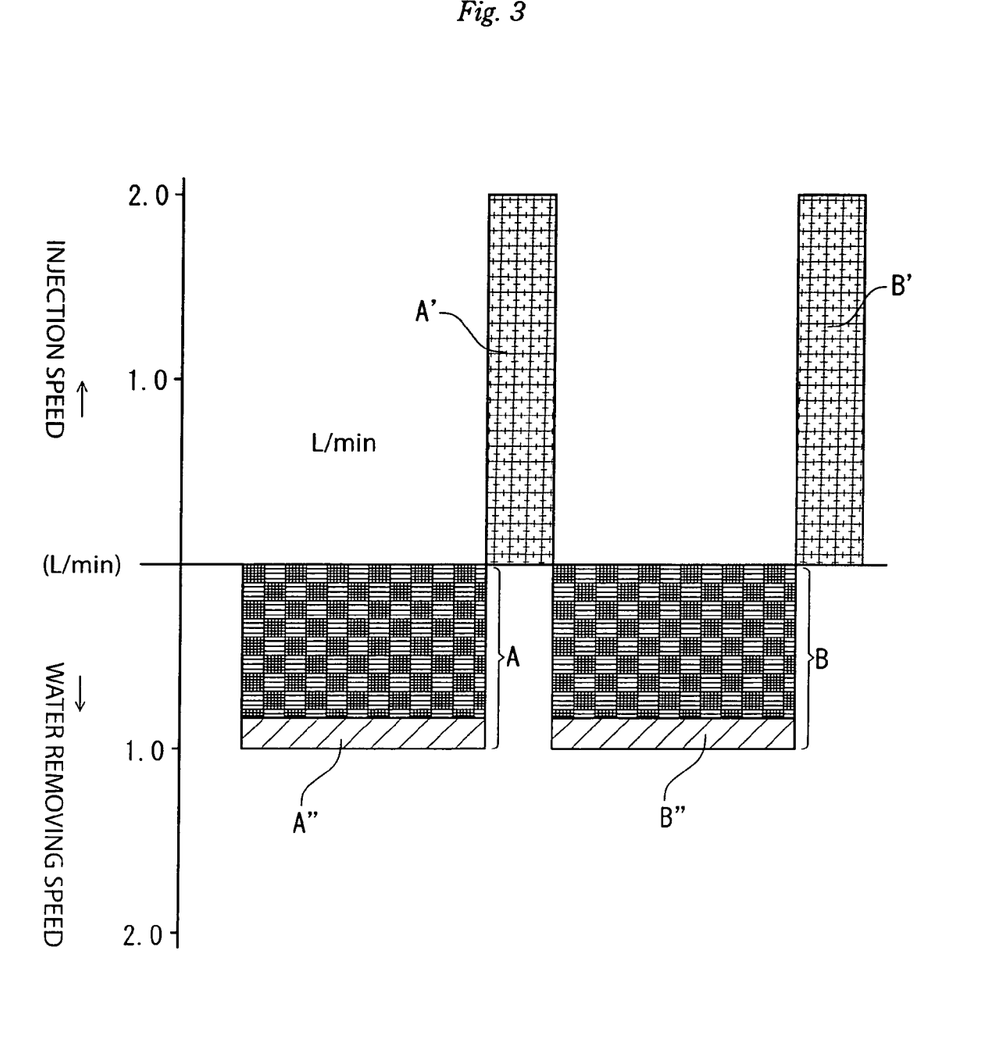
FIG. 3 is a schematic view showing an example of a water removal-injection pattern by the hemodialysis apparatus of the present invention.

As for the input operation of the hemodialysis apparatus, as shown in FIG. 2, when the amount of the removed body fluid and the total amount of the substitution fluid (or the total amount of the injected substitution fluid) are not input, the routine cannot proceed to the next step. However, as for the settings of the treatment time and the number of cycles, even when the treatment time and the number of cycles are not input, default values (i.e., initial values) are already set, and therefore, the operation is controlled with the condition of the initial values. After a screen for confirming whether values to be set are input or not is displayed and the values are confirmed, a pattern composed of the amount of the injected substitution fluid and the amount of the removed body fluid per cycle, and the amount of a fluid discharged by a water removing pump as shown in FIG. 3 is displayed.

Assuming that reference symbol A represents an initial total filtration amount, A' an initial substitution fluid injection amount, A" an initial body fluid removal amount, B a second total filtration amount, B' a second substitution fluid injection amount, and B" a second body fluid removing amount, the total filtration amount, water removing time, substitution fluid injection amount, and substitution fluid injection time in each cycle can be set and changed while the relationships: A=A'+A" and B=B'+B" are maintained.

The change in a water removal-injection pattern is actually performed by the following procedure. The time per cycle and the water removing time required per cycle are automatically calculated by determining (i.e., inputting) a body fluid removing amount, a water removing time, a total substitution fluid amount, and the number of cycles, and consequently, [substitution fluid injection time/cycle]=[time of one cycle]−[water removing time/cycle]−[blank time] is set on a screen.

On this screen, [time of fluid discharge performed by water removing pump/cycle], the amount of the fluid discharged by the water removing pump, and the injecting rate of the substitution fluid are determined by changing [time of substitution fluid injection/cycle] while maintaining the above-mentioned relationship (such that the amount of the injected substitution fluid, the amount of the removed body fluid, and the amount of the fluid discharged by the water removing pump each become constant). On the contrary, [time of substitution fluid injection/cycle] or the like may be changed sequentially by changing and setting [time of fluid discharge performed by water removing pump/cycle].

By changing the setting of the cycle time and [amount of injected substitution fluid/cycle], the amount of the injected substitution fluid can be changed for each cycle. The total time of all the cycles can also be changed. Changes in the amount of the substitution fluid and the time due to changes as described above are reflected on the subsequent cycles, that is, subsequent in terms of time. By changing the pattern per cycle, the remaining cycle patterns are changed to the same pattern as above, or a pattern can be set for each cycle.

Further, the amount of the removed body fluid can also be changed for each cycle according to a body fluid removing pattern obtained by a hematocrit monitor for measuring the hematocrit value or by ultrafiltration.

According to the tidal HDF treatment of the present invention, compared with the ordinary Push & Pull HDF, the substitution fluid injection amount per time is large, so the blood circulation action of a patient may be influenced. Therefore, it is desirable to perform monitoring with an automatic hemadynamometer, a hematocrit monitor, or the like, or to control in association with those monitors. As other safety mechanism, the water removing operation and the substitution fluid injection operation may be stopped by the detection of abnormality with a blood circuit internal pressure, a dialysis fluid pressure, a bubble detector, and the like.

According to the tidal HDF of the present invention, the pressure in the blood circuit may be fluctuated depending upon the injection timing of a substitution fluid. Therefore, it is desirable to separately set a warning reference value of a venous pressure and a dialysis fluid pressure.

Figure 4:
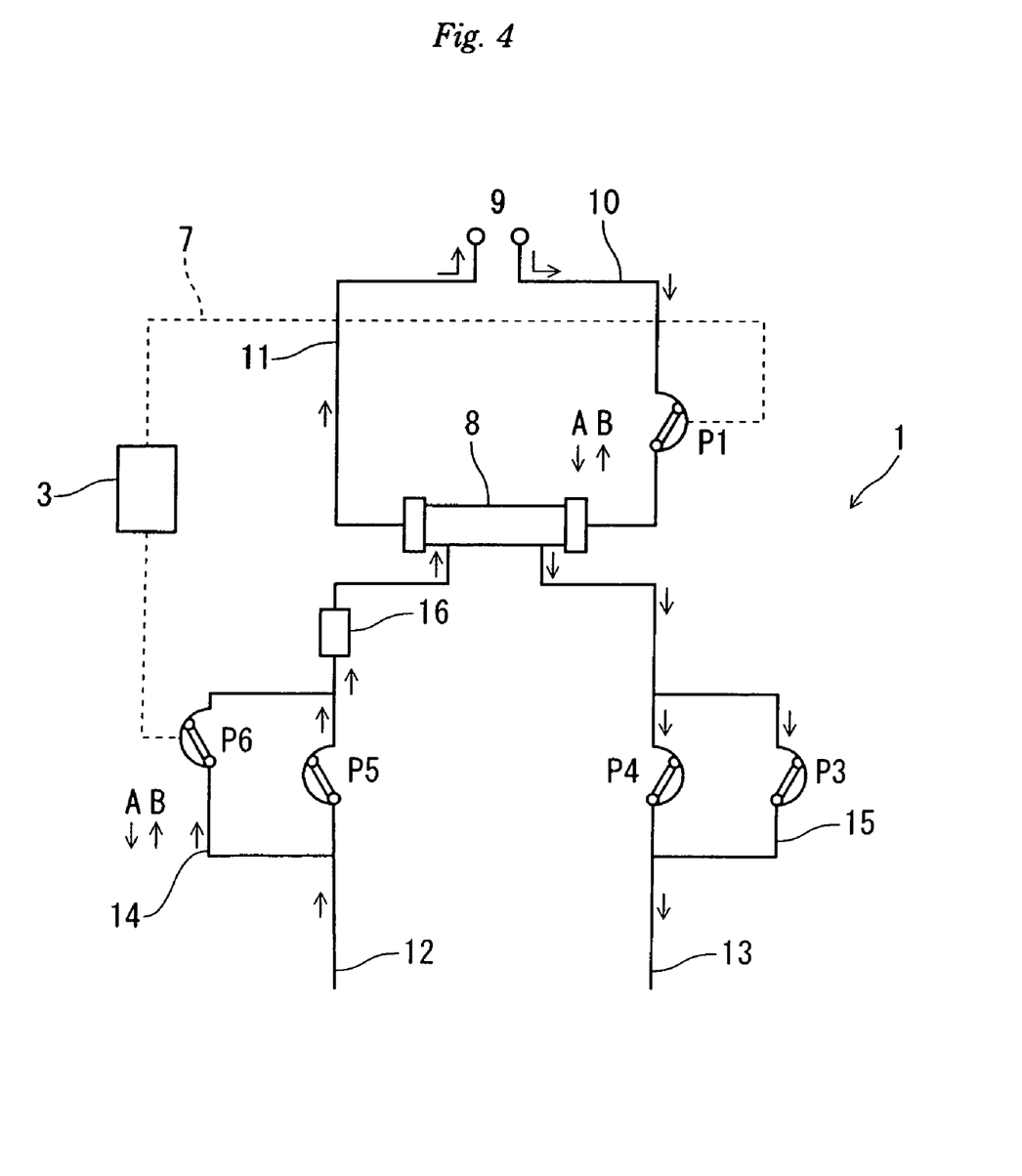
FIG. 4 is a schematic view schematically showing an overall configuration of an exemplary hemodialysis apparatus of the present invention.

Next, FIG. 4 shows a schematic view of the entire hemodialysis apparatus of the present invention.

A hemodiafiltration apparatus 1 includes a hemodialyzer 8 for bringing blood into contact with a dialysis fluid through a translucent membrane to purify the blood, a first blood circuit 10 having a blood pump P1 for guiding the blood taken out from a living body 9 to the dialyzer 8, a second blood circuit 11 having means for guiding the blood refluxing from the dialyzer 8 to the living body 9, a dialysis fluid supply circuit 12 having a dialysis fluid supply pump P5 for guiding a dialysis fluid into the dialyzer 8, and a dialysis fluid discharge circuit 13 having a dialysis fluid discharge pump P4 for discharging the dialysis fluid refluxing from the dialyzer 8. In order to enhance the level of purification of a dialysis fluid, it is desirable to provide an endotoxin removal filter 16 in the dialysis fluid supply circuit 12 on an upstream side of the hemodialyzer 8.

In the hemodialysis apparatus 1, in one or both of a setting portion of the dialysis fluid supply pump P5 of the above-mentioned dialysis fluid supply circuit 12 and a setting portion of the dialysis fluid discharge pump P4 of the dialysis fluid discharge circuit 13, bypass circuits 14 and 15 having fluid feed pumps P3 and P6 different from the above-mentioned pumps are provided, and the fluid feed pumps P3 and P6 provided in the (or these) bypass circuits 14 and 15 and the above-mentioned blood pump P1 can rotate forwardly or backwardly.

Herein, if the fluid feed pump P3 is rotated in the same direction as that of the dialysis fluid discharge pump P4, water removal by filtration is performed. On the contrary, if the fluid feed pump P3 is rotated in the direction opposite to that of the dialysis fluid discharge pump P4, substitution fluid injection by back-filtration is performed. Alternatively, if the fluid feed pump P6 is rotated in the same direction as that of the dialysis fluid supply pump P5, substitution fluid injection by back-filtration is performed. On the contrary, if the fluid feed pump P6 is rotated in the direction opposite to that of the dialysis fluid supply pump P5, water removal by filtration is performed.

The blood pump P1, either or both of the above-mentioned fluid feed pumps P3 and P6 (provided in the bypass circuits), and although not shown, a dialysis working apparatus 2 such as flow path opening/closing means for opening/closing a dialysis fluid circuit and a blood circuit are connected to a control unit 3 through a transmission systems 7 (FIG. 1). The control unit 3 causes either one of the fluid feed pumps P3 and P6 to perform forceful back-filtration via the hemodialyzer 8.

Owing to the back-filtration operation, a dialysis fluid flows in the blood circuit side, and after an elapse of a predetermined period of time, the filtration via the hemodialyzer 8 is performed this time by the fluid feed pump P3 or P6. This filtration operation removes a fluid in the blood circuit to the dialysis fluid side. At this time, the discharge amount is set in such a manner that the fluid feed pump P3 or P6 discharges the amount obtained by adding a body fluid removal amount to the amount of the previously flowed back-filtration fluid (i.e., substitution fluid).

Hereinafter, the present invention will be described by way of embodiments.

As described above, according to the present invention, an operation can be started by inputting the set value in an input unit 4 while confirming the set conditions with the display unit 5. Using the hemodialyzer 8 accommodating hollow yarns, in a dialysis fluid supply and discharge system in which the fluid feed amount of the dialysis fluid supply pump P5 is adjusted to be the same as that of the dialysis fluid discharge pump P4, the fluid feed pump P3 is driven in the same fluid feeding direction as that of the dialysis fluid discharge pump P4, whereby filtration (i.e., water removal) via the hemodialyzer 8 can be performed. Further, the fluid feed pump P3 is driven in the direction opposite to that of filtration (i.e., water removal), whereby back-filtration via the dialyzer 8 can be performed.

Alternatively, if the fluid feed pump P6 is rotated in the same direction as that of the dialysis fluid supply pump P5, substitution fluid injection by back-filtration is performed. On the contrary, if the fluid feed pump P6 is rotated in the direction opposite to that of the dialysis fluid supply pump P5, water removal by filtration is performed. Alternatively, the fluid feed pumps P3 and P6 are controlled in association with each other, whereby a similar operation can be performed.

The flux operation (hereinafter, also referred to as "back-filtration operation") of a fluid from the dialysis fluid side to the blood circuit side by back-filtration is performed at a previously set flux speed and flux amount. The reflux operation (hereinafter, also referred to as "filtration operation") of a fluid from the blood circuit side to the dialysis fluid circuit side by filtration is performed at a previously set reflux speed and reflux amount. The present invention provides a hemodialysis apparatus that repeats such the flux operation and reflux operation intermittently and alternately.

The hemodialysis apparatus of the present invention can take forms of various embodiments as described below while keeping the characteristics thereof.

More specifically, the present invention relates to the above-mentioned hemodialysis apparatus that repeats a filtration operation and a back-filtration operation alternately as described above, thereby efficiently removing a solute.

In the hemodialysis apparatus of the present invention, a blank time, during which neither a filtration operation nor a back-filtration operation is performed, can be provided between the back-filtration operation and the filtration operation. During the blank time, a set value is input in the input unit 4 while it is confirmed with the display unit 5. Thus, a back-filtered fluid is likely to permeate through interstitial tissue or cells.

In the above-mentioned hemodialysis apparatus, the movement amount (i.e., a filtrate amount or a back-filtrate amount) of the fluid in each operation is calculated by the product of the fluid movement speed (i.e., filtration rate or back-filtration rate) in each operation and the time required for each operation. For carrying out the present invention, it is required to calculate the movement amount of a filtrate amount or a back-filtrate amount so as to measure the degree of a hemodiafiltration treatment based on the substitution liquid amount. This makes the setting and control easy.

In the above-mentioned hemodialysis apparatus, when the combination of the filtration operation and the back-filtration operation performed thereafter is defined as one unit (i.e., cycle), the time required for performing a back-filtration operation in each cycle is regulated to be shorter than that for performing a filtration operation in the same cycle. The cycle time per cycle is calculated by the cycle count during the treatment time of hemodialysis (i.e., filtration). In one cycle time, the time of each step is calculated based on the ratio of a previously set filtration time (i.e., water removing time), blank time, and back-filtration time (i.e., injection time). Thus, water can be removed naturally with respect to a living body without giving stress thereto, and further, a solute can be removed efficiently.

In the above-mentioned hemodialysis apparatus, when a total time required for a hemodialysis operation period is defined as a treatment time, then the number of cycles to be performed within the treatment time can be set arbitrarily. The number of cycles is required to be set in accordance with the condition and situation of a patient (the reason for this is that a body fluid removal amount on a treatment date varies every time), and the setting is performed by inputting an input value by the input unit 4 while confirming the input value with the display unit 5. Thus, blood purification processing can be performed in accordance with the condition of a patient and the situation at that time.

When the body fluid amount of a patient to be removed by hemodialysis processing is defined as a body fluid removal amount, the total amount of a fluid flowing in by the back-filtration operation is defined as a total substitution fluid amount, and the number of cycles composed of at least the filtration operation and the back-filtration operation following the filtration operation is defined as a cycle count, in the hemodialysis apparatus, tidal HDF processing is operated or controlled by setting each item of the treatment time, body fluid removal amount, total substitution fluid amount, and cycle count. The set value for each item is input to the input unit 4 while confirming the input value with the display unit 5.

Thus, the treatment appropriate for a patient or the treatment considered to be the best by a doctor can be set minutely.

In the hemodialysis apparatus, the tidal HDF is operated or controlled by inputting the body fluid removal amount and the total substitution fluid amount in the input unit 4. The above-mentioned items are important items that vary depending upon each patient, so the input operation thereof is necessary.

In the case where there is no input of the treatment time or the cycle count, the hemodialysis apparatus is operated or controlled with initial values previously set in the input unit 4. The above-mentioned items hardly influence the treatment although it depends upon a patient, so they can be input only when required. This can omit an input operation, resulting in a reduction in burden on the staff.

The filtration operation and the body fluid removal can be performed by controlling the fluid feed pump P6 and the fluid feed pump P3 in association with each other. More specifically, the filtration operation is performed by the backward rotation of the fluid feed pump P6 or the forward rotation of the fluid feed pump P3, and the back-filtration operation is performed by the forward rotation of the fluid feed pump P6 or the backward rotation of the fluid feed pump P3. In this case, the body fluid removal amount is regulated so that the body fluid removal amount becomes the sum of the injection amount (i.e., minus value) by back-filtration and the discharge amount by filtration.

The filtration operation can be achieved through the water removal by backward rotation of the fluid feed pump P6, and the back-filtration operation can be achieved through the injection by the forward rotation of the fluid feed pump P6. Here, when the water removing amount is set to be equal to the injection amount, the discharge amount of the fluid feed pump P3 is regulated to be the body fluid removal amount.

The filtration operation can be achieved by the backward rotation of the fluid feed pump P6, and the back-filtration operation can be achieved through the injection by the forward rotation of the fluid feed pump P6. Here, when the backward rotation amount of the fluid feed pump P6 per cycle is set to be larger than the forward rotation amount per cycle, and the fluid amount to be filtered by the backward rotation of the fluid feed pump P6 is set to be a total filtration amount (i.e., plus value), the body fluid removal amount is regulated by the sum of the total filtration amount and the injection amount (i.e., minus value).

In the above-mentioned hemodialysis apparatus, in the case where the filtration operation and the back-filtration operation are performed by the fluid feed pump P3 provided in a dialysis fluid circuit, when the amount of a fluid discharged from the dialysis fluid discharge circuit 13 to the outside of the circuit by the fluid feed pump P3 is defined as a pump discharge amount, the pump discharge amount is regulated to be the sum of the filtrate amount (i.e., water removing amount) refluxing from a first blood side circuit to the dialysis fluid discharge side circuit 13 by the filtration operation and the back-filtrate amount (i.e., substitution fluid injection amount) flowing in from the dialysis fluid supply side circuit 12 to a second blood circuit side by the back-filtration operation. Thus, hemodiafiltration is performed under the condition that a set body fluid removal amount is ensured at all times.

In the above-mentioned hemodialysis apparatus, the discharge amount of the fluid feed pump P3 in each cycle is regulated to be the sum of the filtrate amount and the back-filtrate amount in each cycle. The filtrate amount and the back-filtrate amount (i.e., minus value) in each cycle are added and monitored by counting the rotation amount of the fluid feed pump P3. Consequently, in each cycle, hemodiafiltration is performed under the condition that a set water removing amount of a patient is ensured and water removal can be controlled with the passage of time.

In the above-mentioned hemodialysis apparatus, when the amount of water to be removed by an ultrafiltration operation in each cycle is a body fluid removal amount per cycle, the body fluid removal amount per cycle is obtained by dividing the body fluid removal amount equally by the cycle count. This operation is in a stage in which the time and amount of Push and Pull represented by symbol (c) in FIG. 2 are distributed equally, so the body fluid removal amount is also an equal value divided by the cycle count. This simplifies the input operation.

In the above-mentioned hemodialysis apparatus, when the amount of water to be removed by a filtration operation in each cycle is a water removing amount per cycle, the water removing amount per cycle is calculated by the product of the back-filtration rate and the back-filtration time distributed for each cycle. In the case of changing a substitution fluid amount per cycle (i.e., back-filtration rate×injection time), the water removing amount is also changed automatically so as to be equal to a substitution fluid amount. In the case of changing treatment conditions, a body fluid removal pattern is also changed automatically. By re-distributing the body fluid removal amount to each cycle in accordance with the ratio of the period of each cycle of a changed body fluid removal pattern, an input operation is facilitated.

In the above-mentioned hemodialysis apparatus, when the time required for the filtration operation in each cycle is a water removing time per cycle, the amount of fluid to be discharged by a water removing pump by the filtration operation is a pump discharge amount per cycle, the time required for a back-filtration operation in each cycle is a substitution fluid injection time per cycle, and the amount of a fluid flowing in by the back-filtration operation is a substitution fluid (injection) amount, by increasing or decreasing the substitution fluid injection time per cycle, the water removing time per cycle, the water removing amount per cycle, and the pump discharge amount per cycle are set automatically.

In the back-filtration operation, there are two parameters, that is, a back-filtration time and a back-filtrate amount. When one of the parameters (i.e., time) is changed, a speed (amount/time) calculated before the change is made invariable, and the other parameter (i.e., amount) is changed. Regarding this, a value is changed at all times as required by automatic calculation. Thus, automatic setting is performed by automatic calculation using the relationship between two parameters and the calculation results by the parameters. The set parameters are stored in a memory in the apparatus. In this case, an automatic setting pattern can be changed by setting the parameter to be invariable.

Thus, minute measures can be taken in accordance with each patient and the situation at that time. Further, the burden of the input operation on the staff can be alleviated.

In the above-mentioned hemodialysis apparatus, by increasing or decreasing the water removing time per cycle, the substitution fluid injection time per cycle, the substitution fluid injection amount per cycle, and the pump discharge amount per cycle are automatically set as described above. Thus, minute measures can be taken in accordance with each patient and the situation at that time. Further, the burden of the input operation on the staff can be alleviated.

In the above-mentioned hemodialysis apparatus, by increasing or decreasing the substitution fluid injection amount per cycle or the water removing amount per cycle as described above, the substitution fluid amount in each cycle or the water removing amount in each cycle can be changed. Thus, minute measures can be taken in accordance with each patient and the situation at that time. Further, the burden of the input operation on the staff can be alleviated.

In the above-mentioned hemodialysis apparatus, the time required per cycle can be changed arbitrarily in each cycle. Minute measures can be taken in accordance with each patient and the situation at that time.

In the above-mentioned hemodialysis apparatus, when the set state of a water removing time and a water removing amount per cycle, and the set state of a substitution fluid injection time and a substitution fluid amount in the same cycle are defined as a water removal-injection pattern per cycle, in the case where the water removal-injection pattern per cycle is set or changed, the water removal-injection pattern in each cycle, that is, the cycle after the set cycle can be set or changed to the same pattern. Thus, the burden of the input operation on the staff can be alleviated.

In the above-mentioned hemodialysis apparatus, the water removal-injection pattern in each cycle can be changed by the water removing conditions set by hematocrit value measuring means (assay by an optical sensor utilizing the fact that red blood cells, blood platelet, plasma, and the like that are components constituting the blood have peculiar light absorption properties), and by the display of the state of blood from the hematocrit value measuring means. Thus, minute measures can be taken in accordance with each patient and the situation at that time.

In the above-mentioned hemodialysis apparatus, the total filtration-injection pattern in each cycle can be changed in accordance with the body fluid removal conditions set by the body fluid removal program by ultrafiltration. More specifically, this is a method of dividing the body fluid removal amount for hemodialysis (filtration) treatment of that cycle in terms of time, and setting a total filtration rate on a stage basis (on an elapsed time basis), and a function (i.e., program) of automatically changing the total filtration rate as time elapses, and thus, the total filtration rate is set in the input unit 4 while being confirmed with the display unit 5, and is set in an internal memory. Thus, minute measures can be taken in accordance with the state of each patient.

In the above-mentioned hemodialysis apparatus, either or both of the above-mentioned filtration operation and the above-mentioned back-filtration operation is/are performed continuously a plurality of times, and a cycle including a plurality of or one of filtration operations and a plurality of or one of back-filtration operations is repeated at least two times. Thus, more appropriate conditions are set in accordance with the state of each patient, whereby efficient minute measures can be taken.

In the above-mentioned hemodialysis apparatus, the movement amount (i.e., filtrate amount or back-filtrate amount) of a fluid in each operation is calculated by the product of a fluid movement speed (i.e., filtration rate or back-filtration rate) in each operation and the time required for each operation. Because of this, according to the present invention, the input, setting, and control operations can be performed easily.

INDUSTRIAL APPLICABILITY

As described above, the apparatus according to the present invention is suitable for a dialysis apparatus for efficiently removing wastes and moisture from a body of a patient to purify blood by performing filtration and back-filtration periodically and intermittently.

The invention claimed is:
1. A method of hemodialysis performed by a hemodialyzer apparatus, the apparatus comprising:

a hemodialyzer for bringing blood into contact with a dialysis fluid through a translucent membrane to purify the blood;

a first blood circuit having a blood pump for guiding blood taken out from a living body into the hemodialyzer;

a second blood circuit having means for guiding the blood refluxing from the hemodialyzer to the living body;

a dialysis fluid supply circuit having a dialysis fluid supply pump for guiding the dialysis fluid into the hemodialyzer;

a dialysis fluid discharge circuit having a dialysis fluid discharge pump for discharging the dialysis fluid refluxing from the hemodialyzer;

at least one bypass circuit having a fluid feed pump capable of rotating forwardly and backwardly, wherein each one of the at least one bypass circuit is coupled to one of either the dialysis fluid supply circuit or the dialysis fluid discharge circuit to bypass, respectively, the dialysis fluid supply pump or the dialysis fluid discharge pump; and a controller for controlling hemodialyzer operations; the method comprising the steps of:

alternately repeating a back-filtration operation and a filtration operation with an intermediary blank time therebetween, during which neither the filtration operation nor the back-filtration operation are performed;

the controller rotating the fluid feed pump in the same direction as the direction of a direction of the dialysis fluid supply pump for a back-filtration operation when the bypass circuit bypasses the dialysis fluid supply circuit;

the controller rotating the fluid feed pump in the opposite direction as a direction of the dialysis fluid discharge pump for a back-filtration operation when the bypass circuit bypasses the dialysis fluid discharge circuit;

the controller rotating the fluid feed pump in the opposite direction as the direction of a direction of the dialysis fluid supply pump for a filtration operation when the bypass circuit bypasses the dialysis fluid supply circuit;

the controller rotating the fluid feed pump in the same direction as a direction of the dialysis fluid discharge pump for a filtration operation when the bypass circuit bypasses the dialysis fluid discharge circuit; and the controller pausing rotation of the fluid feed pump for the blank time to allow back-filtered fluid to enter the living body.

2. The hemodialysis method according to claim 1, wherein, when a body fluid amount of a patient to be removed by hemodialysis processing is defined as a body fluid removal amount, a total amount of a fluid flowing in by the back-filtration operation is defined as a total substitution fluid amount, and number of cycles within a treatment time composed of the alternating back-filtration operations and filtration operations with intermediary blank times is defined as a cycle count, further comprising the step of setting each item of the treatment time, the body fluid removal amount, the total substitution fluid amount, and the cycle count.

3. The hemodialysis method according to claim 1, further comprising the step of setting input values for a body fluid removal amount and a total substitution fluid amount.

4. The hemodialysis method according to claim 1, further comprising regulating the body fluid removal amount in each of the cycles so that the body fluid removal amount corresponds to either one of an injection amount or a discharge amount from the fluid feed pump.

5. The hemodialysis method according to claim 1, further comprising regulating, when the back-filtration operation is performed by the fluid feed pump provided in the dialysis fluid discharge circuit, the fluid feed pump discharge amount to be a sum of a total filtration amount refluxing by the filtration operation and a back filtration amount flowing in by the back-filtration operation.

6. The hemodialysis method according to claim 1, further comprising regulating body fluid removal amount in each cycle to be a sum of an injection amount from the fluid feed pump and a total filtration amount.

7. The hemodialysis method according to claim 1, further comprising regulating fluid feed pump discharge amount in each cycle to be a sum of a filtrate amount and a back-filtrate amount.

8. The hemodialysis method according to claim 1, in which a time required for the filtration operation in each cycle is defined as a water removing time per cycle, an amount of a fluid discharged by the fluid feed pump in the same filtration operation is defined as the fluid feed pump discharge amount per cycle, a time required for the back-filtration operation in each of the cycles is defined as an injection time per cycle, and an amount of a fluid flown in by the back-filtration operation is defined as the substitution fluid amount per cycle, and further comprising automatically setting the water removing time per cycle, a water removing amount per cycle, and the pump discharge amount per cycle by increasing or decreasing the injection time per cycle.

9. The hemodialysis method according to claim 8, further comprising setting injection time per cycle, an injection amount per cycle, and the fluid feed pump discharge amount per cycle by increasing or decreasing the water removing time per cycle.

10. The hemodialysis method according to claims 8 or 9, further comprising changing either one or both of the water removing amount per cycle or the injection amount per cycle by increasing or decreasing either one or both of the injection amount per cycle or the water removing amount per cycle.

11. A hemodialysis apparatus, comprising:

a hemodialyzer for bringing blood into contact with a dialysis fluid through a translucent membrane to purify the blood;

a first blood circuit having a blood pump for guiding blood taken out from a living body into the hemodialyzer;

a second blood circuit having means for guiding the blood refluxing from the hemodialyzer to the living body;

a dialysis fluid supply circuit having a dialysis fluid supply pump for guiding the dialysis fluid into the hemodialyzer;

a dialysis fluid discharge circuit having a dialysis fluid discharge pump for discharging the dialysis fluid refluxing from the hemodialyzer;

at least one bypass circuit having a fluid feed pump capable of rotating forwardly and backwardly, wherein each one of the at least one bypass circuit is coupled to one of either the dialysis fluid supply circuit or the dialysis fluid discharge circuit to bypass, respectively, the dialysis fluid supply pump or the dialysis fluid discharge pump;

a controller for controlling said fluid feed pump rotation, wherein said controller is configured to alternately repeat a back-filtration operation and a filtration operation with an intermediary blank time therebetween, during which neither the filtration operation nor the back-filtration operation are performed, the blank time having a duration which allows back-filtered fluid to enter the living body;

wherein the controller is configured to rotate the fluid feed pump in the same direction as the direction of a direction of the dialysis fluid supply pump for a back-filtration operation when the bypass circuit bypasses the dialysis fluid supply circuit;

wherein the controller is configured to rotate the fluid feed pump in the opposite direction as a direction of the dialysis fluid discharge pump for a back-filtration operation when the bypass circuit bypasses the dialysis fluid discharge circuit;

wherein the controller is configured to rotate the fluid feed pump in the opposite direction as the direction of a direction of the dialysis fluid supply pump for a filtration operation when the bypass circuit bypasses the dialysis fluid supply circuit; and wherein the controller is configured to rotate the fluid feed pump in the same direction as a direction of the dialysis fluid discharge pump for a filtration operation when the bypass circuit bypasses the dialysis fluid discharge circuit.

12. The hemodialysis apparatus according to claim 11, wherein the controller is configured to control a period of time for rotating the fluid feed pump in the back filtration operation to be shorter than a period of time for rotating the fluid feed pump in the filtration operation.

13. The hemodialysis apparatus of claim 11 or 12, wherein the dialysis fluid supply circuit comprises an endotoxin removal filter.

14. The hemodialysis apparatus of claim 11 or 12, further comprising an input unit that sets duration of the blank time.

* * * * *